(12) United States Patent
Takeda et al.

(10) Patent No.: US 7,052,135 B2
(45) Date of Patent: May 30, 2006

(54) OPHTHALMOLOGIC APPARATUS

(75) Inventors: Takanori Takeda, Tokyo (JP); Masaki Ohno, Tokyo (JP); Tomoyoshi Abe, Tokyo (JP); Toshihiro Koyama, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 333 days.

(21) Appl. No.: 10/393,367

(22) Filed: Mar. 21, 2003

(65) Prior Publication Data

US 2003/0184712 A1    Oct. 2, 2003

(30) Foreign Application Priority Data

Mar. 26, 2002    (JP)    ............... 2002-086875

(51) Int. Cl.
*A61B 3/00* (2006.01)
*A61B 3/10* (2006.01)

(52) U.S. Cl. ............... 351/245; 351/200; 351/205; 351/221

(58) Field of Classification Search ........... 351/200, 351/205, 206, 211, 212–216, 221, 222, 224, 351/225, 245, 246
See application file for complete search history.

(56) References Cited

U.S. PATENT DOCUMENTS

| | | | | |
|---|---|---|---|---|
| 5,424,788 A | * | 6/1995 | Satake et al. ............... | 351/206 |
| 5,488,443 A | * | 1/1996 | Ota et al. .................. | 351/245 |
| 5,619,290 A | * | 4/1997 | Nakayama et al. ......... | 351/245 |
| 6,072,623 A | * | 6/2000 | Kitajima et al. ............. | 351/221 |
| 6,283,596 B1 | * | 9/2001 | Yoshimura et al. ......... | 351/214 |
| 6,337,993 B1 | * | 1/2002 | Kishida et al. .............. | 351/221 |
| 6,361,167 B1 | * | 3/2002 | Su et al. ..................... | 351/206 |
| 6,364,484 B1 | * | 4/2002 | Yamada ...................... | 351/200 |
| 6,409,134 B1 | * | 6/2002 | Oddsen, Jr. ................ | 248/274.1 |
| 2001/0023914 A1 | * | 9/2001 | Oddsen .................... | 248/274.1 |
| 2002/0163624 A1 | * | 11/2002 | O'Brien et al. ............. | 351/245 |

* cited by examiner

*Primary Examiner*—Ali Imam
*Assistant Examiner*—John R Sanders
(74) *Attorney, Agent, or Firm*—Armstrong, Kratz, Quintos, Hanson & Brooks, LLP

(57) ABSTRACT

Disclosed is an ophthalmologic apparatus, such as a slit lamp microscope, which is improved in terms of cable routing when an imaging apparatus is used, thereby achieving an improvement in operability for the examiner, mitigating the bother or discomfort for the subject, and realizing an improved outward appearance. In a slit lamp microscope using cables for electrical connection between an imaging apparatus and an image processing system or a control system, there is provided a cable hole having an opening provided with at least two curved corners through which cables connected to the imaging apparatus come together and which is formed so as to enclose partially the near portion of the protrusive axle shell of the base, or there is provided a cable routing path in which the cables connected to the imaging apparatus are routed by way of an accommodating groove with a detachable cover provided on the front side of the support arm, a cable hole provided in a protrusive axle shell of a base protruding toward a chin rest stand from a pedestal, a cable hole of the chin rest stand, and a cable hole provided in a table, to be passed under the table.

6 Claims, 17 Drawing Sheets

OPHTHALMOLOGIC APPARATUS

BACKGROUND OF THE INVENTION

1. Field of the Invention

The present invention relates to an ophthalmologic apparatus, such as a slit lamp microscope.

2. Related Background Art

A slit lamp microscope, which is used as a kind of ophthalmologic apparatus for ophthalmology, has been used.

In a slit lamp microscope, slit-like illumination light, or slit light, and background illumination light for illuminating the entire eye to be examined, are applied from an illumination system supported on a pedestal installed on a table to the eye to be examined which is secured in position by setting the chin of the subject on a chin rest stand arranged upright on an end of the table, and a slit image of the eye (e.g., a corneal cross section image) is observed by an observation optical system supported on the pedestal through the intermediation of a support arm so as to be horizontally rotatable, and, further, the slit image and an overall image of the eye are picked up by using an imaging apparatus, such as a video camera, mounted to the observation optical system to turn them into visual images by using an image processing apparatus or the like.

To operate the imaging apparatus and transmit an image of the eye to the image processing apparatus or the like, it is naturally necessary to electrically connect the imaging apparatus, the power source portion for supplying power, and the image processing apparatus or the like for image processing through cables, such as a power cable and a signal transmission cable.

In the conventional slit lamp microscope, when using an imaging apparatus involving cable connection, no special measures are taken regarding the routing path for the cables. Cables, one end of each of which is connected to the imaging apparatus, are passed by exposed routing along the observation optical system and the pedestal and led under the table by way of the lower portion of the chin rest stand provided upright on an end of the table, that is, by way of the vicinity of the subject, to be connected to the image processing apparatus or the like.

Thus, when using an imaging apparatus involving cable connection in the observation system, the cables, which are in exposed routing, will come into contact with the observation system when the examiner tries to change the apparatus position relative to the eye to be examined by horizontally rotating the observation system, resulting in a deterioration in operability for the examiner.

Further, the cables, which are exposed in the region below the chin rest stand, may come into contact with the knee, etc. of the subject, causing him to experience a bother or discomfort.

Furthermore, due to the exposed routing of the cables, the slit lamp microscope as a whole offers a rather disorderly appearance.

SUMMARY OF THE INVENTION

The present invention has been made in view of the above problems in the prior art. It is an object of the present invention to provide an ophthalmologic apparatus which is endowed with a novel contrivance to route the cables when using an imaging apparatus in the observation system, thereby achieving an improvement in operability for the examiner, mitigating the bother or discomfort for the subject, and improving the overall appearance of the apparatus.

In order to solve the above-mentioned problems, according to a first aspect of the present invention, there is provided an ophthalmologic apparatus including: an illumination system for illuminating an eye to be examined; a support arm for supporting an observation system for observing the eye to be examined and an imaging apparatus mounted to the observation system; a base for rotatably supporting the illumination system, the observation system, and the support arm on a protrusive axle shell; a pedestal for supporting the base; a chin rest stand for securing the eye to be examined of a subject in position; and a table on which the pedestal is installed and to an end of which the chin rest stand is mounted, the ophthalmologic apparatus using cables which are connected at one end to the imaging apparatus and the other ends of which are guided under the table for electrical connection between the imaging apparatus and an image processing system or a control system, the apparatus being characterized in that there is provided a cable hole having an opening through which cables connected the imaging apparatus come together and which is provided so as to enclose partially the neighbor of the protrusive axle shell of the base.

According to a second aspect of the invention, in the first aspect of the present invention, the ophthalmologic apparatus is characterized in that in the cable hole provided near the protrusive axle shell of the base is provided with at least two corner portions of the opening as being curved along the outer periphery of the cylinder portion of the protrusive axle shell, and displacement of the cables according to the manner of rotation of the observation system and the imaging apparatus with respect to the base is regulated by the smooth corners.

According to this second aspect of the invention, displacement of the cables according to the rotation of the observation system and the imaging apparatus with respect to the base is regulated by the smooth corners of the cable hole provided along the protrusive axle shell of the base, whereby it is possible to prevent the cables from being bent or damaged when the observation system and the imaging apparatus rotate with respect to the base.

According to a third aspect of the present invention, an arbitrary configuration of an opening can be formed as such sector like, square, triangular etc., which can give cables a room to play within it when the observation system and the imaging system rotate, and two curved corners are connected as being curved with each other so as the cables to be settled in either corner with respect to the position of the protrusive axle shell of the base.

In accordance with the fourth aspect of the present invention, there is provided the cable routing path in which the cables are led by way of the accommodation groove with the detachable cover provided on the front side of the support arm, the cable hole formed in the protrusive axle shell of the base protruding toward the chin rest stand from the pedestal, the cable hole of the chin rest stand, and the cable hole of the table, to be passed under the table. Therefore, when an imaging apparatus is used in the observation system, the cables connected to the imaging apparatus are accommodated in the accommodation groove with the detachable cover provided on the front side of the support arm, and led under the table by way of the cable hole provided in the protrusive axle shell of the base, the cable hole of the chin rest stand, and the table hole provided in the table, to be connected to an apparatus which is to be connected to the imaging apparatus.

As a result, the cables connected to the imaging apparatus are not exposed on the examiner side, thereby achieving an improvement in terms of operability for the examiner. Further, due to the construction in which the cables are passed through the cable hole of the chin rest stand and the cable hole provided in the table, the cables do not come into contact with a part of the body of the subject, such as the knee, thereby mitigating the bother or discomfort for the subject. Further, due to the cable routing path, the cables can be laid neatly, thereby achieving an improvement in terms of outward appearance.

According to a fifth aspect of the present invention, in the fourth aspect of the present invention, the ophthalmologic apparatus is characterized in that the detachable cover covering the accommodating groove for the cables, which is provided on the front side of the support arm, has a cable passage port situated at a left-hand side position or a right-hand side position in correspondence with the arrangement of the imaging apparatus added to the observation system and the cable connecting position.

According to the fifth aspect of the invention, a detachable cover is selected which has a cable passing port differing in position according to the arrangement of the imaging apparatus added to the observation system and the cable connecting position, whereby it is possible to effect cable routing in correspondence with various imaging apparatuses.

According to a sixth aspect of the invention, in one of the first through fourth aspects of the present invention, the cables are characterized in that they are a power cable, an image monitor cable, and a signal transmission cable.

According to the sixth aspect of the invention, it is possible to obtain each effect according to the above aspects of the invention when using an imaging apparatus of using a power cable, an image monitor cable, and a signal transmission cable.

DESCRIPTION OF THE PREFERRED EMBODIMENT

Figure 1:
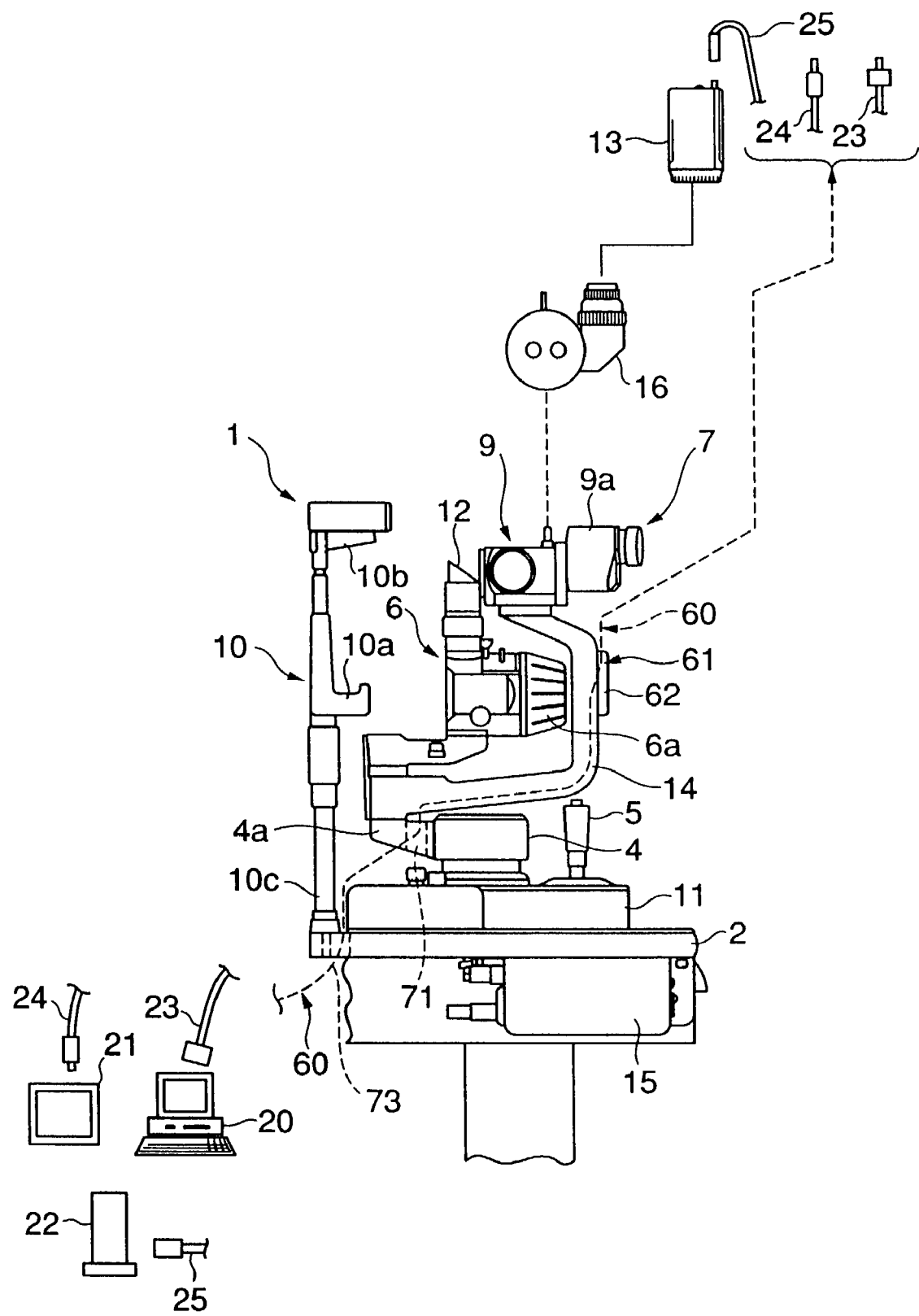
FIG. 1 is a schematic side view showing the construction of a slit lamp microscope according to an embodiment of the present invention.

An embodiment of the present invention will now be described. A slit lamp microscope 1 shown in FIG. 1 constitutes an ophthalmologic apparatus according to this embodiment. It is equipped with a pedestal 11 which is supported on an ophthalmoscopic table 2 so as to be movable horizontally in the lateral and longitudinal directions by a movement mechanism portion 3, a base 4 supported in the vertical direction by the pedestal 11, an operating handle 5 for displacing the pedestal 11 horizontally in the lateral and longitudinal directions through tilting operation, a light source portion 6a supported so as to be horizontally rotatable by a protrusive axle shell 4a of the base 4, an illumination system 6 having a prism 12, etc., an observation system 7 for observing an eye E to be examined, and a chin rest stand 10 having a chin rest 10a for the subject opposed to a barrel main body 9 accommodating the objective lens of the observation system 7, a forehead holder lob, and a base portion 10c mounted to the table 2. The observation system 7 is supported by a support arm 14 which is substantially reverse-L shaped in side view and axially supported by the protrusive axle shell 4a of the base 4.

Figure 2:
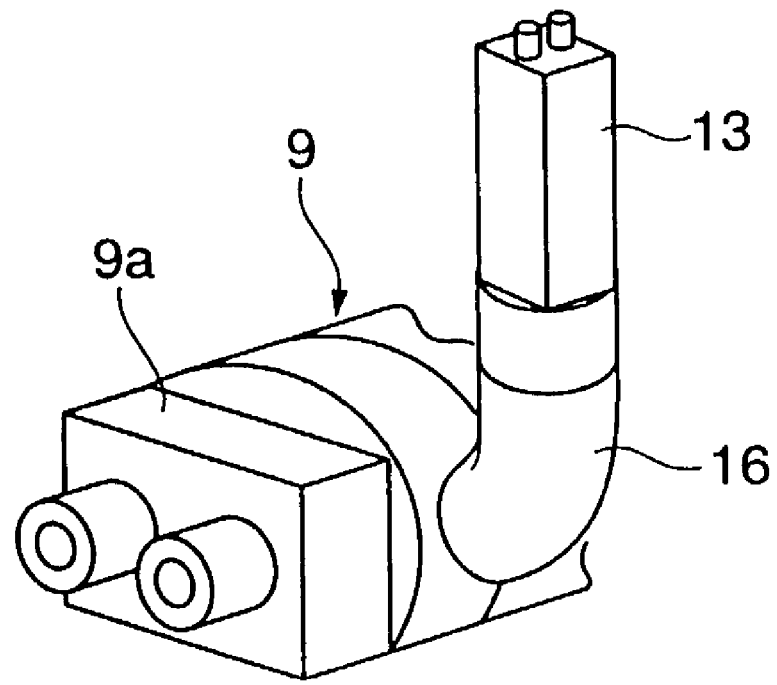
FIG. 2 is a perspective view of an imaging apparatus mounted to the observation system of the slit lamp microscope of this embodiment.

As shown in FIG. 2, an imaging apparatus 13, such as a video camera, is mounted to the barrel main body 9 through the intermediation of a camera attachment 16 with a round outer periphery.

Arranged on the lower side of the table 2 is a power box 15 for supplying power to the light source portion 6a.

Apart from the slit lamp microscope 1, there are arranged an image processing apparatus (computer apparatus) 20 for performing image processing on the image of the eye E, an image monitor 21 for monitoring the image of the eye E, and a power source apparatus 22 for the imaging apparatus 13.

And, the imaging apparatus 13 and the image processing apparatus 20 are connected by a signal transmission cable 23, the imaging apparatus 13 and the image monitor 21 are connected by an image monitor cable 24, and the imaging apparatus 13 and the power source apparatus 22 are connected by a power cable 25.

As indicated by the dotted line in FIG. 1, the slit lamp microscope 1 is equipped with a cable routing path 60 for accommodating and passing the above-mentioned three cables.

This cable routing path 60 will be described with reference to FIGS. 3 through 14. The cable routing path 60 is formed such that the three cables are routed by way of the interior of an accommodating groove 14a with a detachable cover 61 (See FIG. 5) provided on the front side (the examiner side) of the support arm 14, a cable hole 71 provided in the protrusive axle shell 4a of the base 4 protruding toward the chin rest stand 10 from the pedestal 11 (See FIGS. 9 and 10), a cable hole 72 provided in the base portion 10c of the chin rest stand 10 (See FIGS. 11 and 12), and a cable hole 73 provided in the table 2 (See FIG. 16), to be passed under the table 2.

The accommodating groove 14a of the support arm 14, constituting the cable routing path 60, and the detachable cover 61, will be described with reference to FIGS. 3 through 6.

Figure 3:
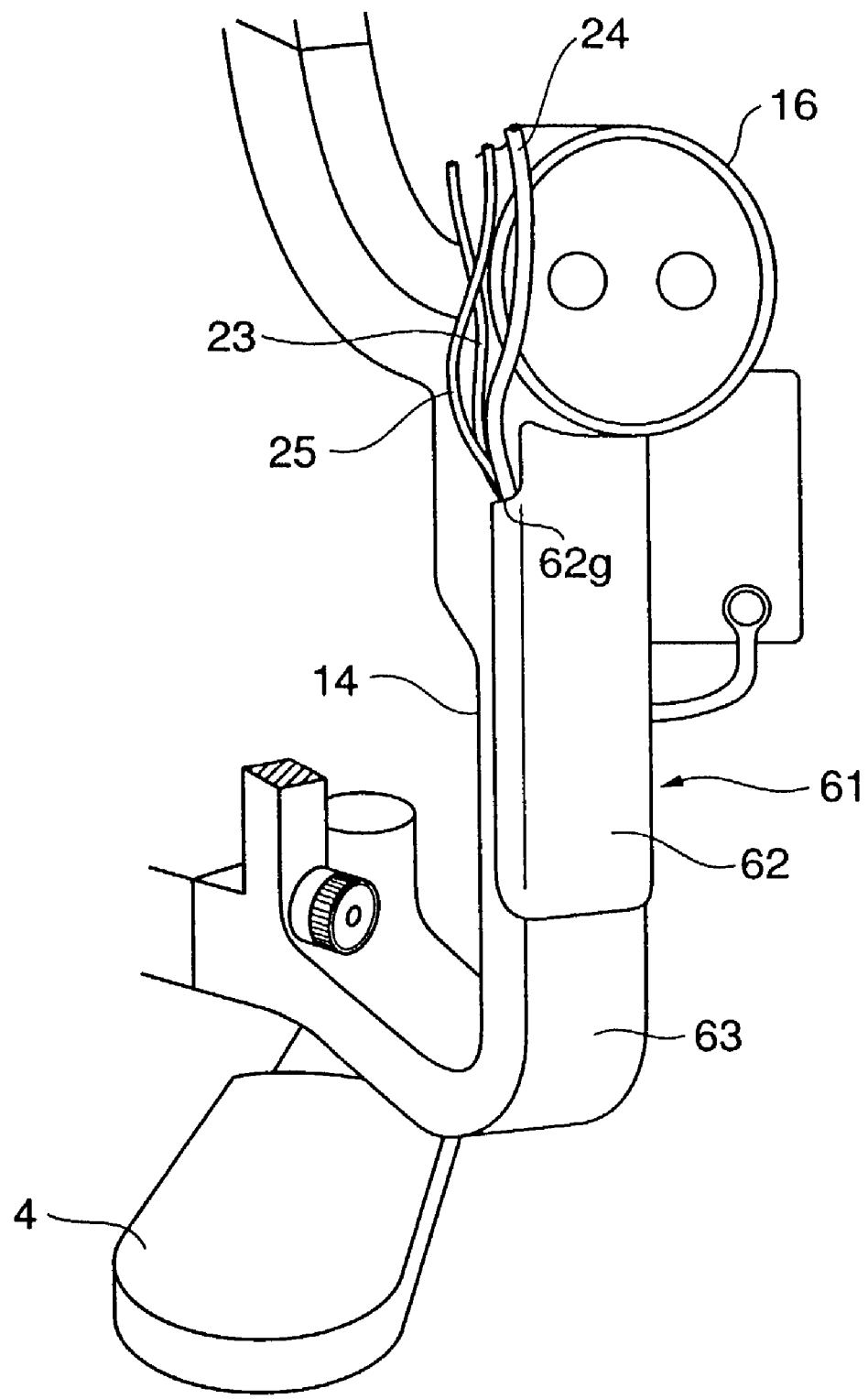
FIG. 3 is a perspective view showing upper and lower covers of this embodiment mounted to the front side of a support arm.
Figure 4:
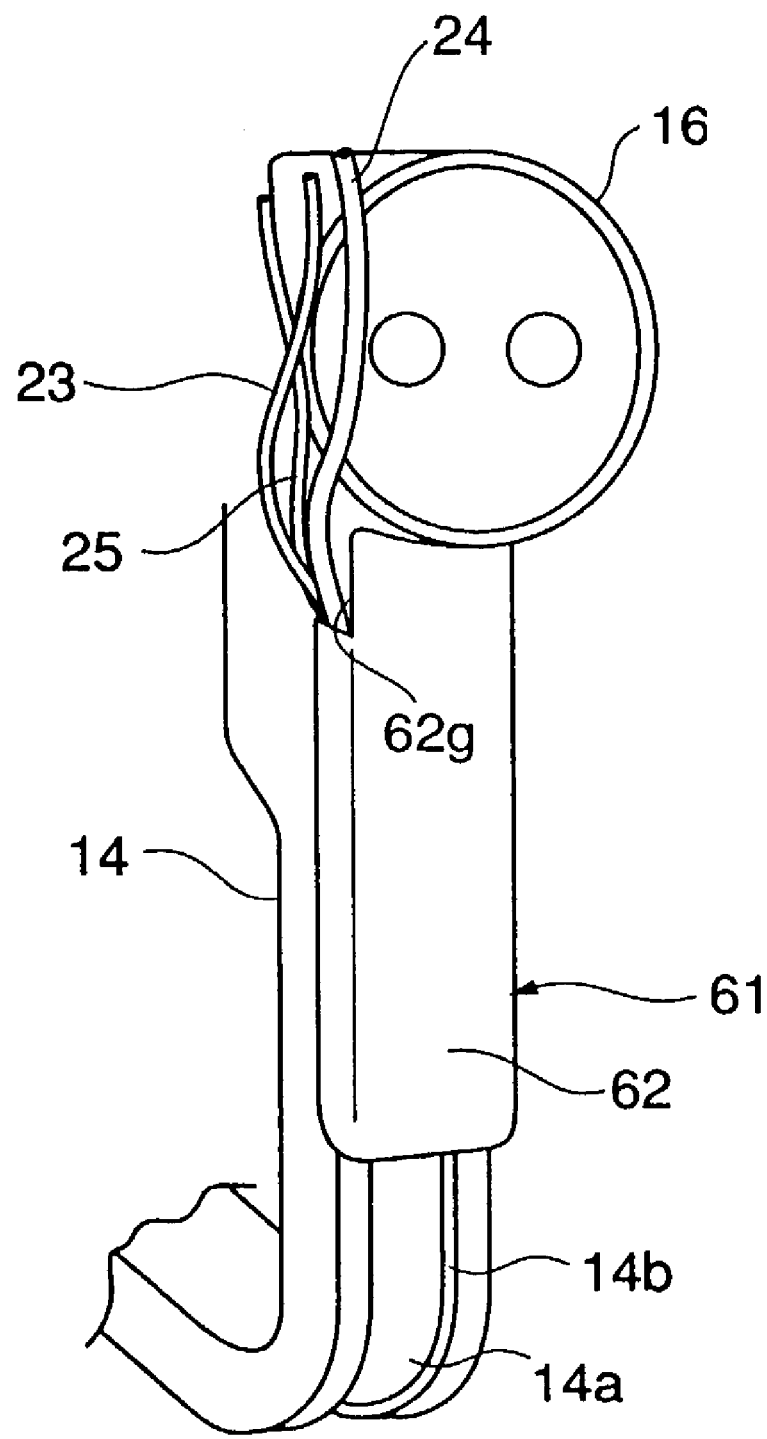
FIG. 4 is a perspective view showing a state in which only the upper cover of this embodiment is mounted to the front side of the support arm.
Figure 5:
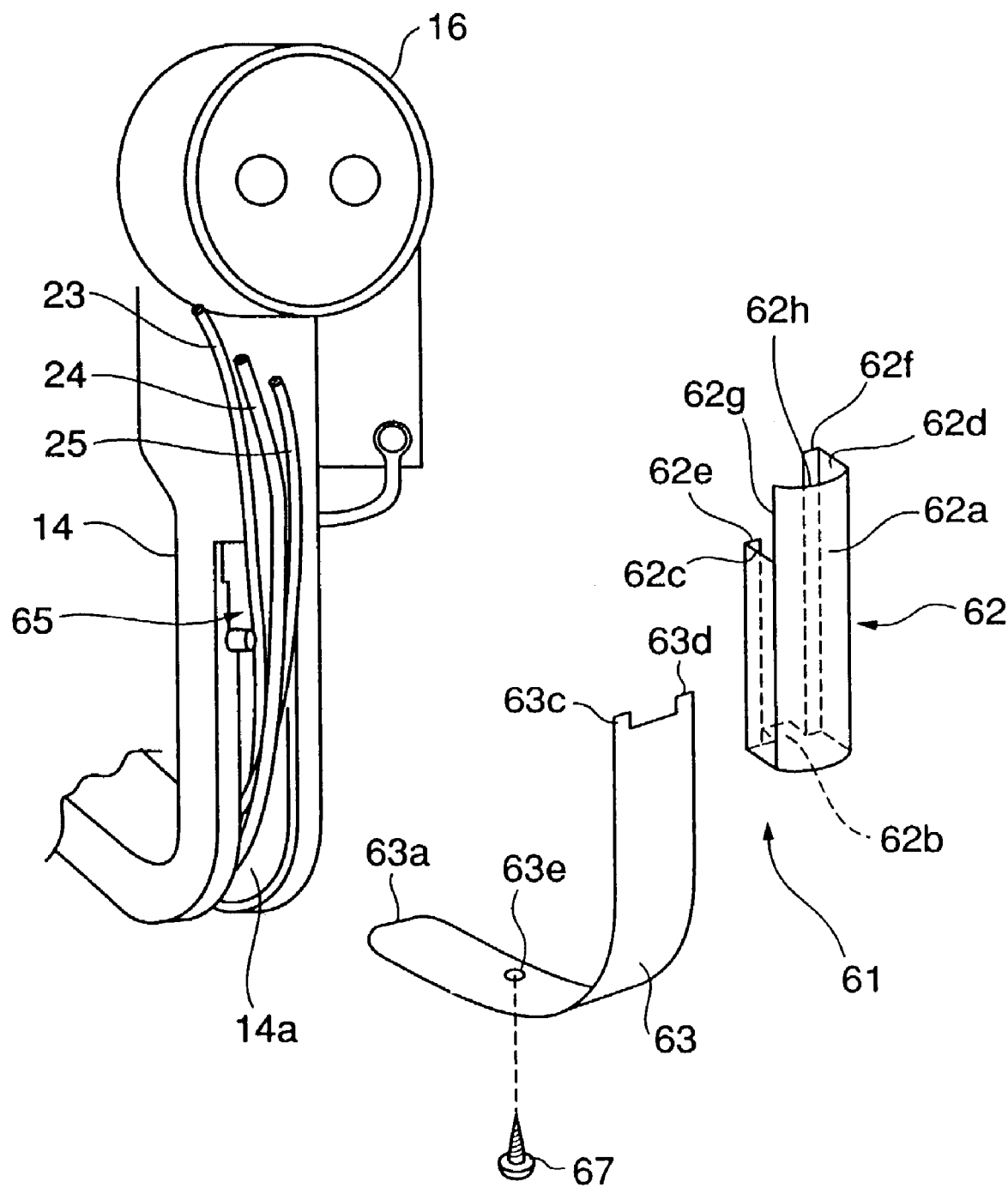
FIG. 5 is a perspective view showing the state in which the upper and lower covers of this embodiment are not mounted to the support arm yet.

The detachable cover 61 is composed of two parts: an upper cover 62 attached to the upper portion of the front side of the support arm 14 and a lower cover 63 attached to the lower portion of the front side of the support arm 14. FIG. 3 shows the state in which the upper cover 62 and the lower cover 63 are attached to the front side of the support arm 14, FIG. 4 shows the state in which only the upper cover 62 is attached to the front side of the support arm 14, FIG. 5 shows the state in which the upper cover 62 and the lower cover 63 have not been attached to the support arm 14 yet, and FIG. 6 shows the accommodating groove 14a on the front side of the support arm 14 and a bracket 65 for the upper cover 62.

The accommodating groove 14a of the support arm 14 is formed by hollowing out the thick-walled portion of the substantially reverse-L-shaped support arm 14 in conformity with its configuration, starting from a position near the protrusive axle shell 4a of the base 4 to a predetermined position in the vertically raised portion of the support arm 14, and is capable of accommodating the cables consisting of the signal transmission cable 23, the image monitor cable 24, and the power cable 25.

Further, throughout the outer periphery of the accommodating groove 14a, there is formed, inwardly from the surface of the support arm 14, a recipient step portion 14b for the attachment of the lower cover 63 and the attachment of the bracket 65 for the upper cover 62 described below, in a depth corresponding to the thickness of the lower cover 63.

Figure 6:
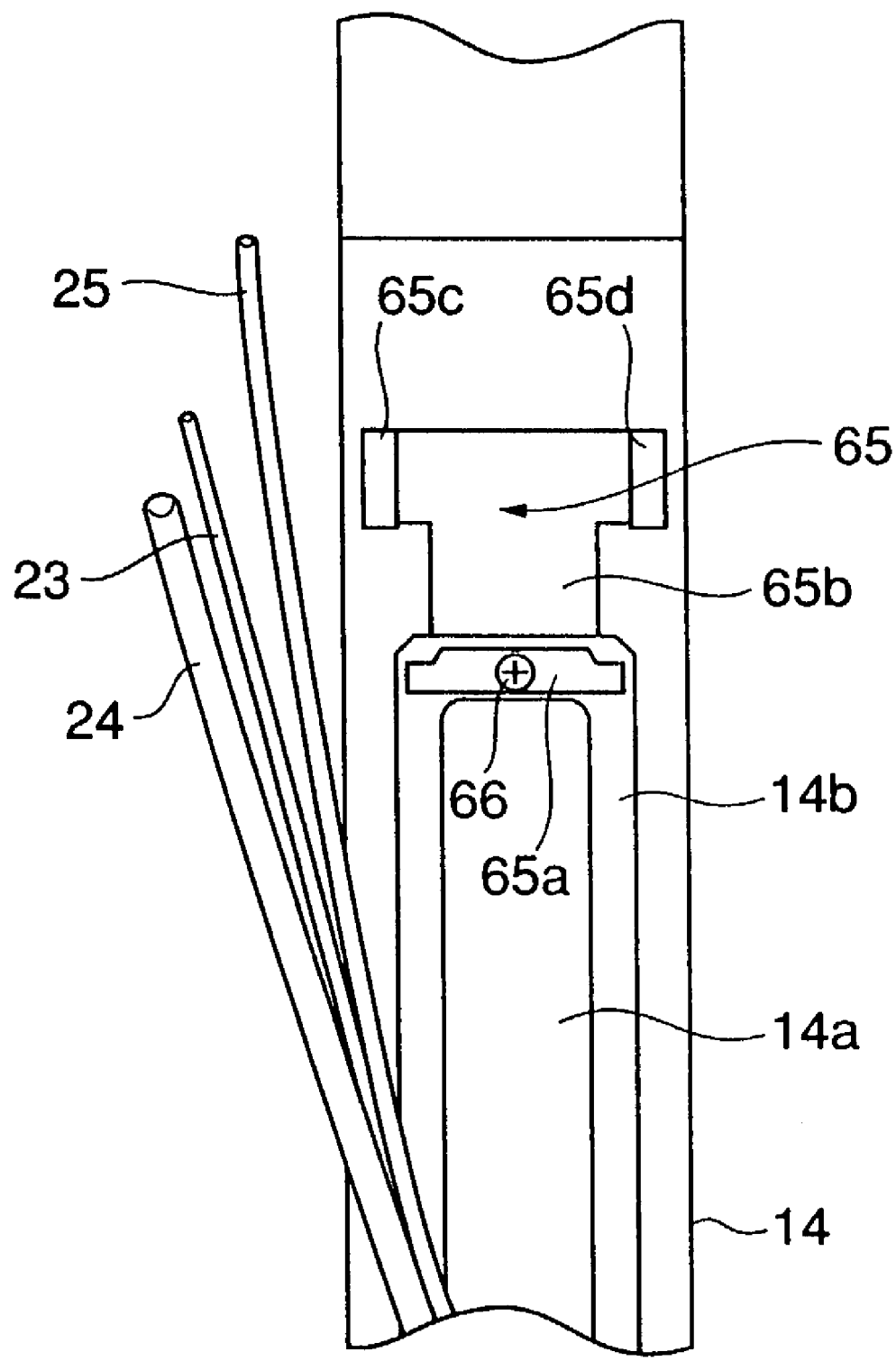
FIG. 6 is an enlarged view showing an accommodating groove on the front side of the support arm of this embodiment and a bracket for the upper cover.

As shown in FIG. 6, the bracket 65 for the upper cover 62 is composed of a mounting piece 65a substantially T-shaped in plan view and fixed to the top portion of the recipient step portion 14b by means of a screw 66, a joint portion 65b joined to the surface of the support arm 14, and a pair of upper cover receiving members 65c and 65d protruding sidewise from the upper portion of the joint portion 65b, the bracket 65 as a whole having a substantially T-shaped configuration in plan view.

The pair of upper cover receiving members 65c and 65d are bent into an L-shape so as to extend away from the joint portion 65b toward the back side of the upper cover 62, exhibiting a rectangular configuration as seen from the back side of the upper cover 62.

And, by snapping the upper cover 62 onto the pair of upper cover receiving members 65c and 65d, the upper cover 62 is attached and fixed to the back side of the support arm 14. It is possible to adopt a construction in which an engagement member 62f of the upper cover 62 described below is pressurized by an elastic plate member (not shown) to thereby prevent wobbling of the upper cover 62.

As shown in FIG. 5, the upper cover 62 attached to the upper portion of the front side of the support arm 14 is formed as a substantially rectangular box open on the support arm 14 side, and is equipped with a rectangular back wall 62a, side walls 62c and 62d bent at 90 degrees with respect to the back wall 62a, engagement members 62e and 62f formed by inwardly bending the distal end portions of the side walls 62c and 62d so as to be opposed to each other, a position regulating protrusion 62b formed at the lower end of the back wall 62a, and a cable passage port 62g provided in the upper portion of one side wall 62c. The upper edge 62h of the back wall 62a is arcuate in conformity with the outer peripheral configuration of the camera attachment 16.

Figure 7:
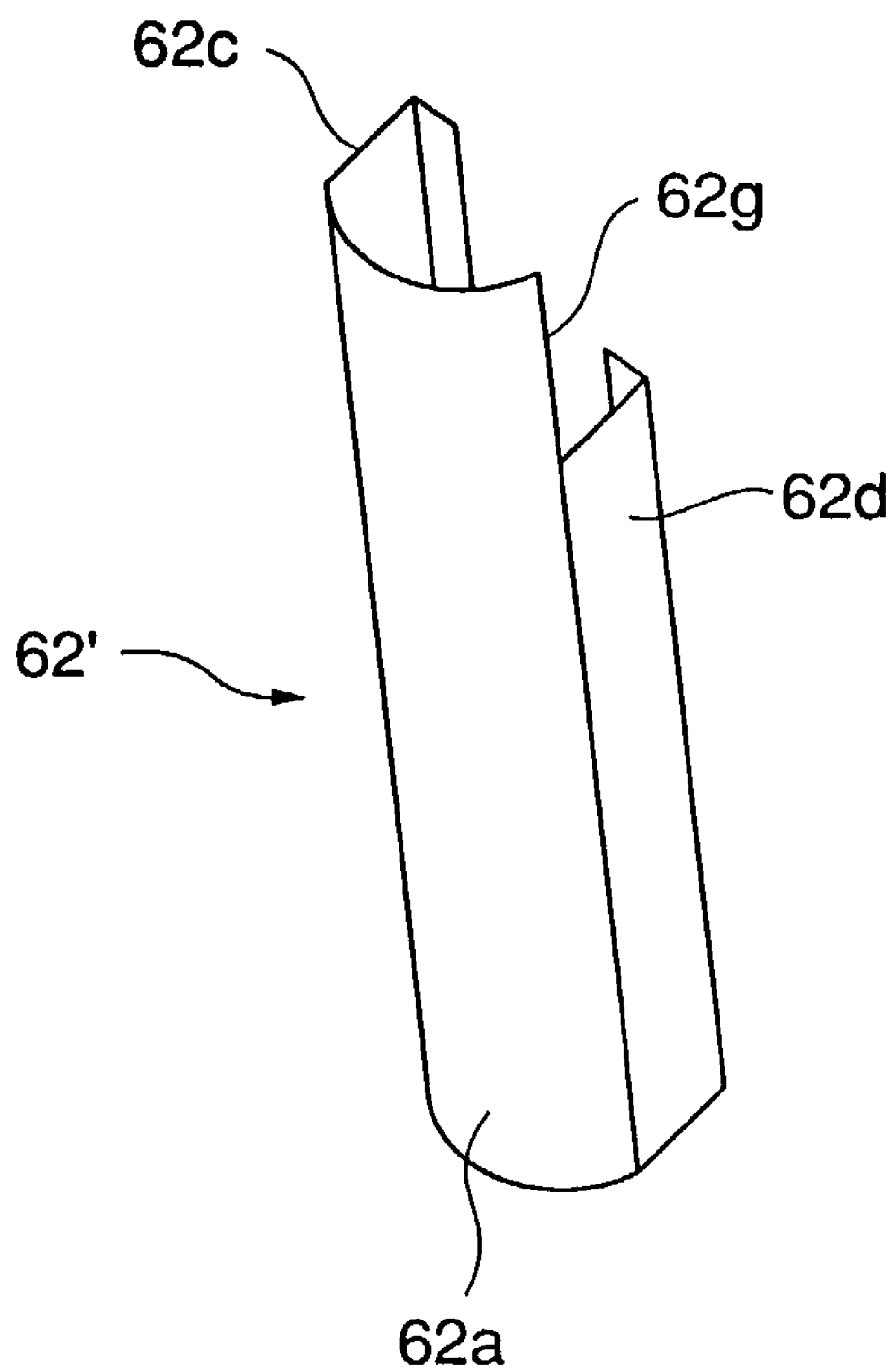
FIG. 7 is a perspective view showing another example of the upper cover of this embodiment.

While in this example the upper cover 62 has the cable passage port 62g on the left-hand side as seen in FIG. 5, it is also possible to adopt an upper cover 62' as shown in FIG. 7 having the cable passage port 62g on the right-hand side. From these upper covers 62 and 62', the optimum one is selected according to the arrangement of the imaging apparatus 13 in the observation system and the cable connecting position.

As shown in FIG. 5, the lower cover 63 attached to the lower portion of the front side of the support arm 14 is mounted to the recipient step portion 14b from the front side of the support arm 14 and covers the cables accommodated in the accommodating groove 14a. In mounting the lower cover 63 to the recipient step portion 14b, the lower cover 63 is applied to the recipient step portion 14b, and a screw 67 is passed through a screw hole 63e provided near one edge of the lower cover 63 to be threadedly engaged with a screw hole provided at the corresponding position in the recipient step portion 14b.

One end 63a of the lower cover 63 extends up to a position near the protrusive axle shell 4a of the base 4 where it does not interfere with the passage of the cables from the accommodating groove 14a to the base 4 side.

As shown in FIG. 5, at the other end 63b of the lower cover 63, there are formed a pair of position regulating protrusions 63c and 63d. When attaching the upper cover 62 after the mounting of the lower cover 63 to the recipient step portion 14b, the pair of position regulating protrusions 63c and 63d regulate the position of the lower portion of the upper cover 62, with the position regulating protrusion 62b being therebetween.

Next, the cable hole 71 provided in the protrusive axle shell 4a of the base 4 and constituting the cable routing path 60, will be described with reference to FIGS. 8 through 11.

Figure 8:
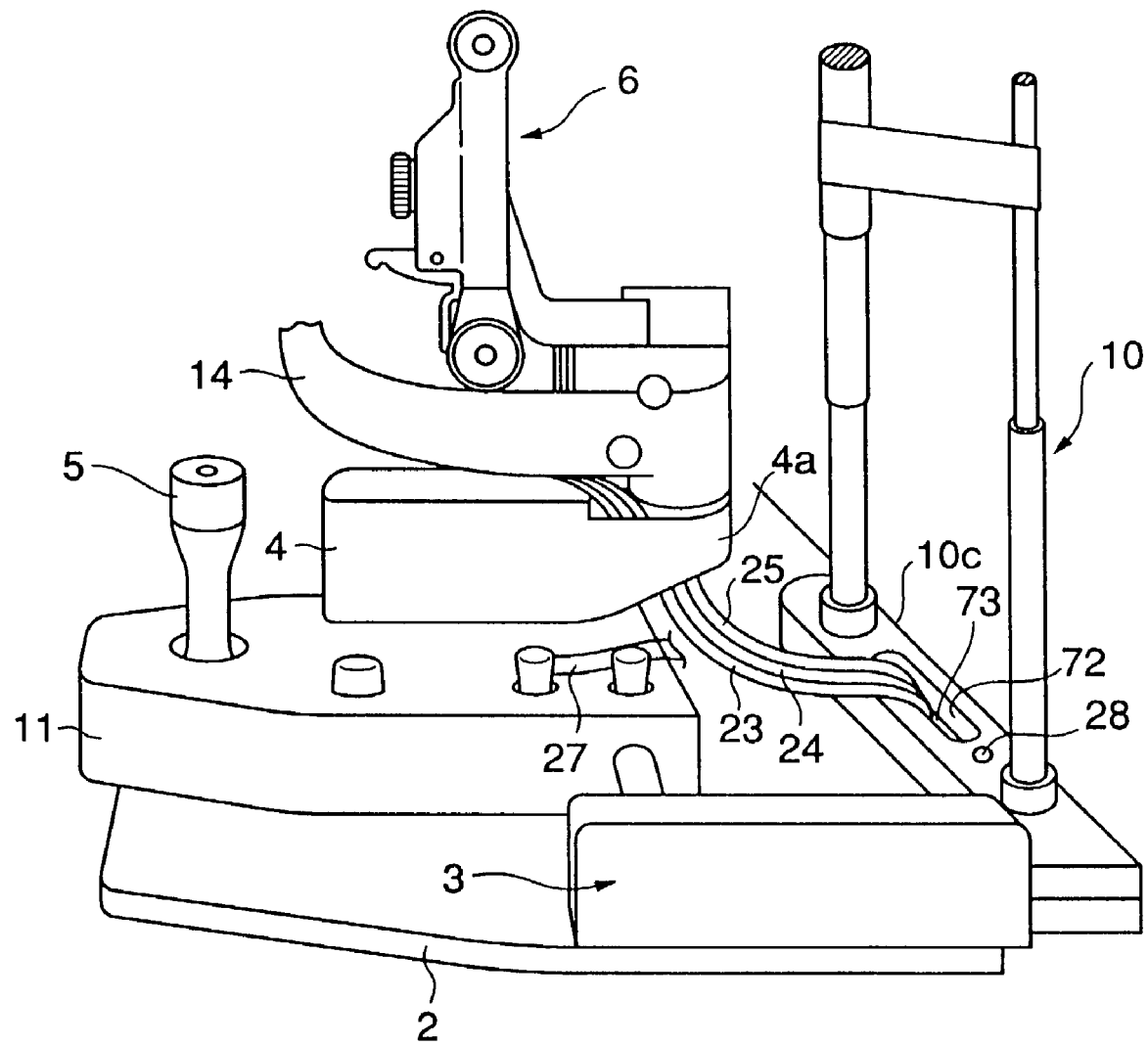
FIG. 8 is a schematic perspective view showing a cable routing path leading from the support arm to a position under the table of the slit lamp microscope of this embodiment.
Figure 9:
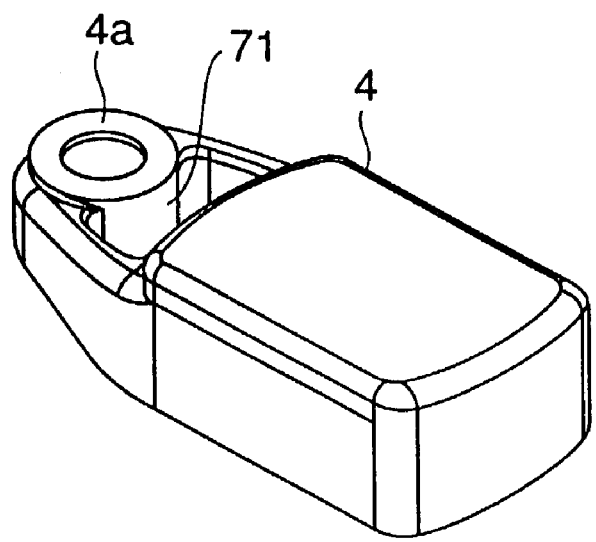
FIG. 9 is a perspective view of a base of this embodiment.
Figure 10:
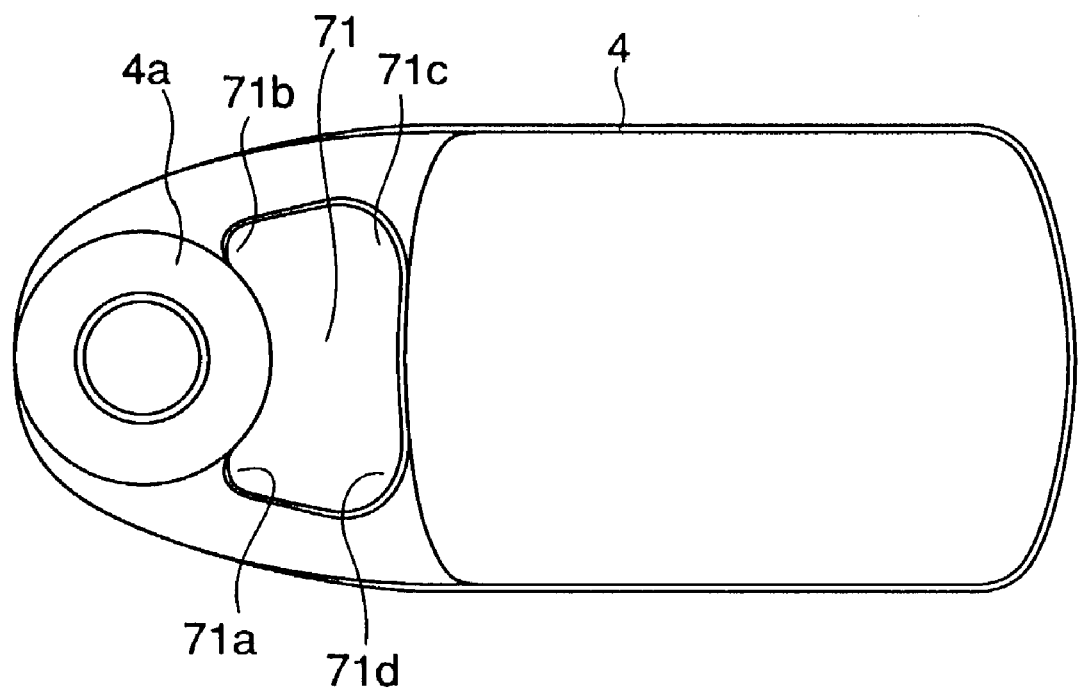
FIG. 10 is a plan view of the base of this embodiment.
Figure 11:
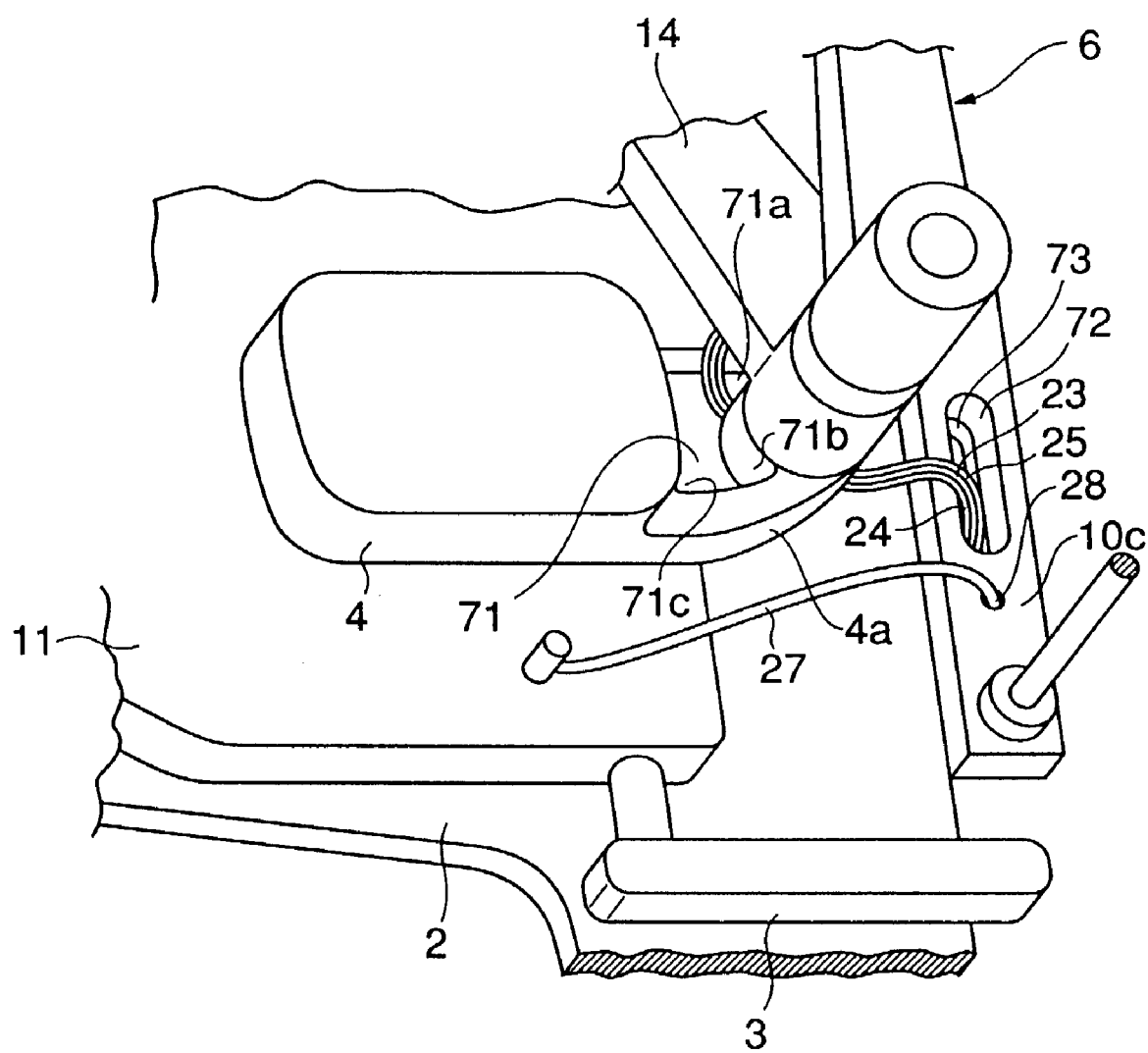
FIG. 11 is a partial perspective view showing a state in which the support arm has been rotated to the left with respect to the base of this embodiment.

The cable hole 71 in this embodiment provided in the protrusive axle shell 4a of the base 4, shown in FIG. 8, is formed as a sector shaped opening which is not limited to this configuration and may be anyway open along the outer periphery of the cylinder portion of the protrusive axle shell 4a, as shown in FIG. 9. The hole 71 is characterized in as shown in the enlarged view of FIG. 10, all the four corners 71a, 71b, 71c, and 71d of this cable hole 71 are smoothly curved. Due to the smooth corners 71a through 71d, in particular, the corners 71a and 71b, when the cables under the accommodating groove 14a are displaced according to the manner of rotation of the observation system 7 and the imaging apparatus 13 with respect to the base 4, positional regulation is effected by playing in the opening appropriately on the cables without damaging or bending the cables. FIG. 11 shows a state in which the support arm 14 supporting the observation system 7 and the imaging apparatus 13 has been rotated to the left with respect to the eye E to be examined. In this case, the cables are displaced to the corner 71a side of the cable hole 71, undergoing positional regulation by this corner 71a so as not to suffer damage or bending. Although not shown, in a state in which the support arm 14 is rotated to the right with respect to the eye E, the cables are displaced to the corner 71b side of the cable hole 71, undergoing positional regulation by this corner 71b.

Next, with reference to FIGS. 12 through 16, the cable holes 72 and 73 constituting the cable routing path 60 will be described. The cable hole 72 for passing the cables is provided in the base portion 10c of the chin rest stand 10, and the cable hole 73 for passing the cables is provided in the table 2.

Figure 12:
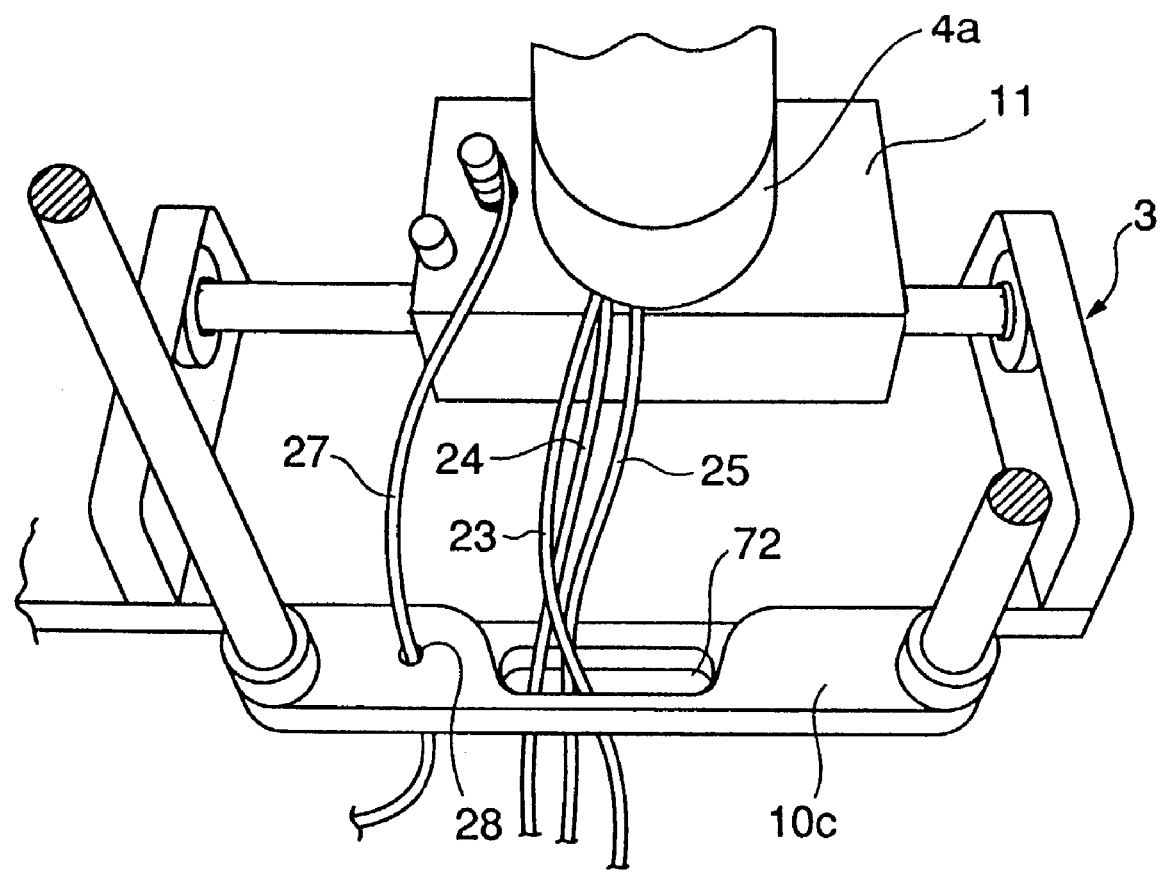
FIG. 12 is a schematic perspective view showing a cable routing path leading from the base to the position under the table of the slit lamp microscope of this embodiment.
Figure 13:
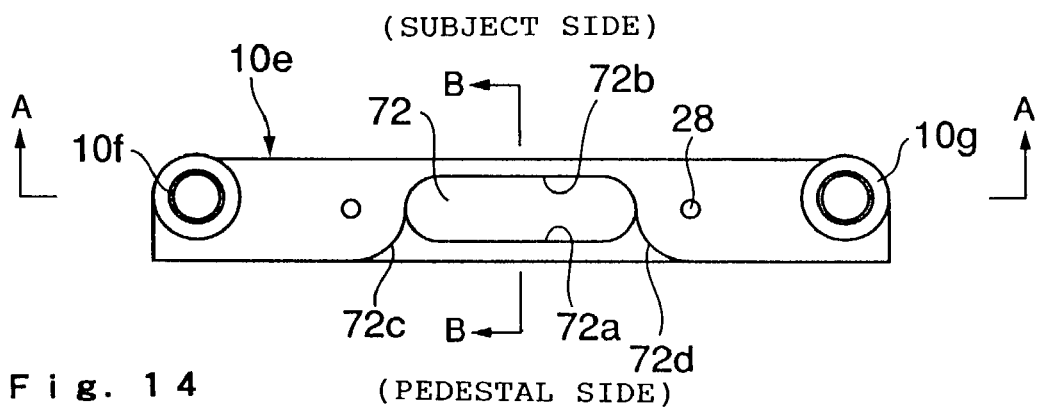
FIG. 13 is a plan view showing the base portion of a chin rest stand of this embodiment.
Figure 14:
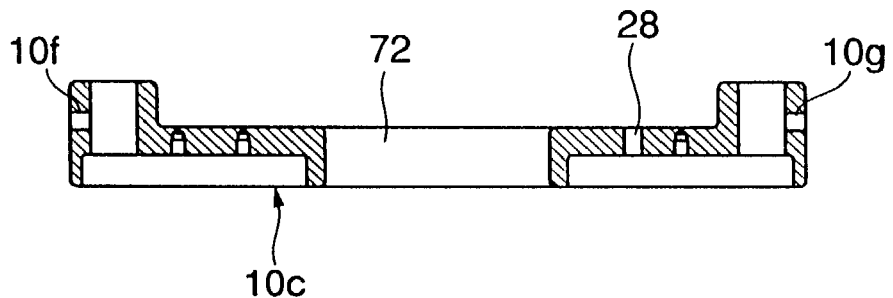
FIG. 14 is a sectional view taken along the line A-A of FIG. 13.
Figure 15:
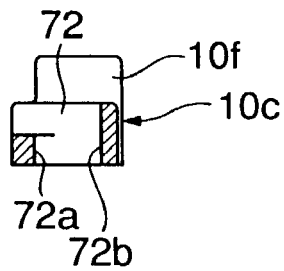
FIG. 15 is a sectional view taken along the line B-B of FIG. 13.

The base portion 10c of the chin rest stand 10 is substantially rectangular, and has at its ends recipient cylinder portions 10f and 10g into which columns 10d and 10e are to be inserted. Further, at the center of the base portion 10c, there is provided the cable hole 72 in the form of an elongated hole with semicircular ends. As shown in FIGS. 12, 13, and 15, the outer periphery of the cable hole 72 has an uneven parallel construction in plan view, with the portion on the pedestal 11 side being a small size thick-walled portion 72a and the portion on the subject side being a large size thick-walled portion 72b. Further, as shown in FIGS. 12 and 13, the upper surface of the pedestal side thick-walled portion 72a is formed so as to have divergent portions 72c and 72d diverging arcuately toward the ends. Due to this configuration of the divergent portions 72c and 72d, even when the pedestal 11 are operated to the right and left on the table 2 to cause displacement of the cables to the right and left, the cables are prevented from suffering damage or bending. The base portion 10c is further equipped with a passage hole 28 for a light quantity adjusting cable 27.

Figure 16:
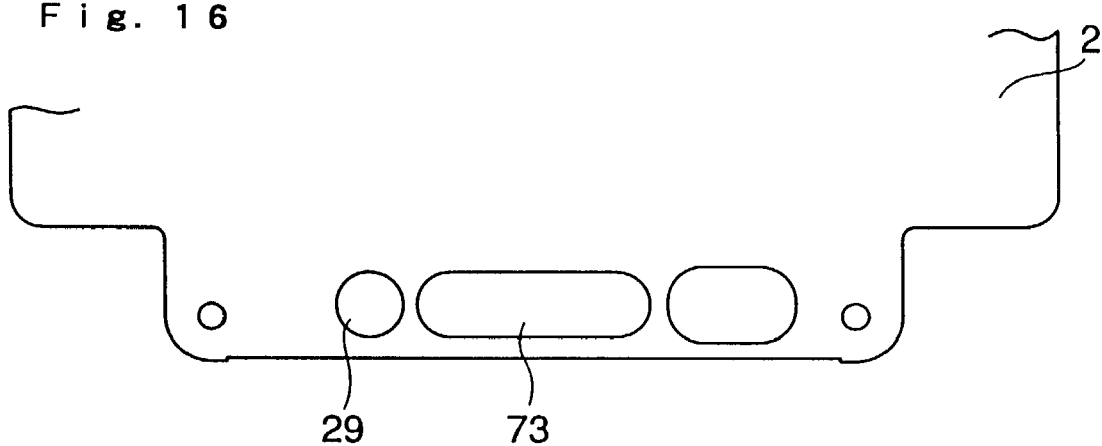
FIG. 16 is a partial enlarged view of the table of this embodiment.

As shown in FIG. 16, the cable hole 73 provided in the table 2 is, in conformity with the configuration of the cable 72, formed as an elongated hole of the same size with semicircular end portions. Further, the table 2 is also provided with a passage hole 29 for a light quantity adjusting cable 27.

Although not shown, instead of providing the cable holes 72 and 73, it is also possible to provide the base portion 10c of the chin rest stand 10 and the subject-side end portion of the table 2 with grooves large enough to accommodate the cables and having no corners. This arrangement advantageously eliminates the need for the operation of passing the cables through the cable holes.

In the above construction, there is provided the cable routing path 60 for routing the cables by way of the interior of the accommodating groove 14a with the detachable cover 61 provided on the front side of the support arm 14, the cable hole 71 provided in the protrusive axle shell 4a of the base 4 protruding toward the chin rest stand 10 from the pedestal 11, the cable hole 72 of the chin rest stand 10, and the cable hole 73 provided in the table 2 before passing them under the table 2. Thus, when the imaging apparatus 13 is used in the observation system 7, the cables connected to the imaging apparatus 13 are accommodated in the accommodating groove 14a with the detachable cover 61 provided on the front side of the support arm 14, and are passed through the cable hole 71 provided in the protrusive axle shell 4a of the base 4, the cable hole 72 of the chin rest stand 10, and the cable hole 73 provided in the table 2 before being led under the table 2 to be connected to various apparatuses connected to the imaging apparatus 13.

As a result, the cables connected to the imaging apparatus 13 are not exposed on the examiner side, making it possible to achieve an improvement in operability for the examiner. Further, due to the construction in which the cables are passed through the cable hole 72 of the chin rest stand 10 and the cable hole 73 provided in the table 73, there is no fear of the cables coming into contact with a part of the body of the subject, such as the knee, thereby eliminating or mitigating the bother or discomfort for the subject. Further, for the apparatus as a whole, due to the cable routing path 60, the cables can be routed neatly, thereby achieving an improvement in the outward appearance.

Further, by selecting the upper cover 62, which is one of the detachable covers 61 and which has the cable passage port 62g differing in position according to the arrangement of the imaging apparatus 13 added to the observation system 7 and the cable connecting position, it is possible to perform cable routing in conformity with different imaging apparatuses 13.

Next, the construction of the optical system of the slit lamp microscope 1 will be described with reference to FIGS. 17 through 23.

Figure 17:
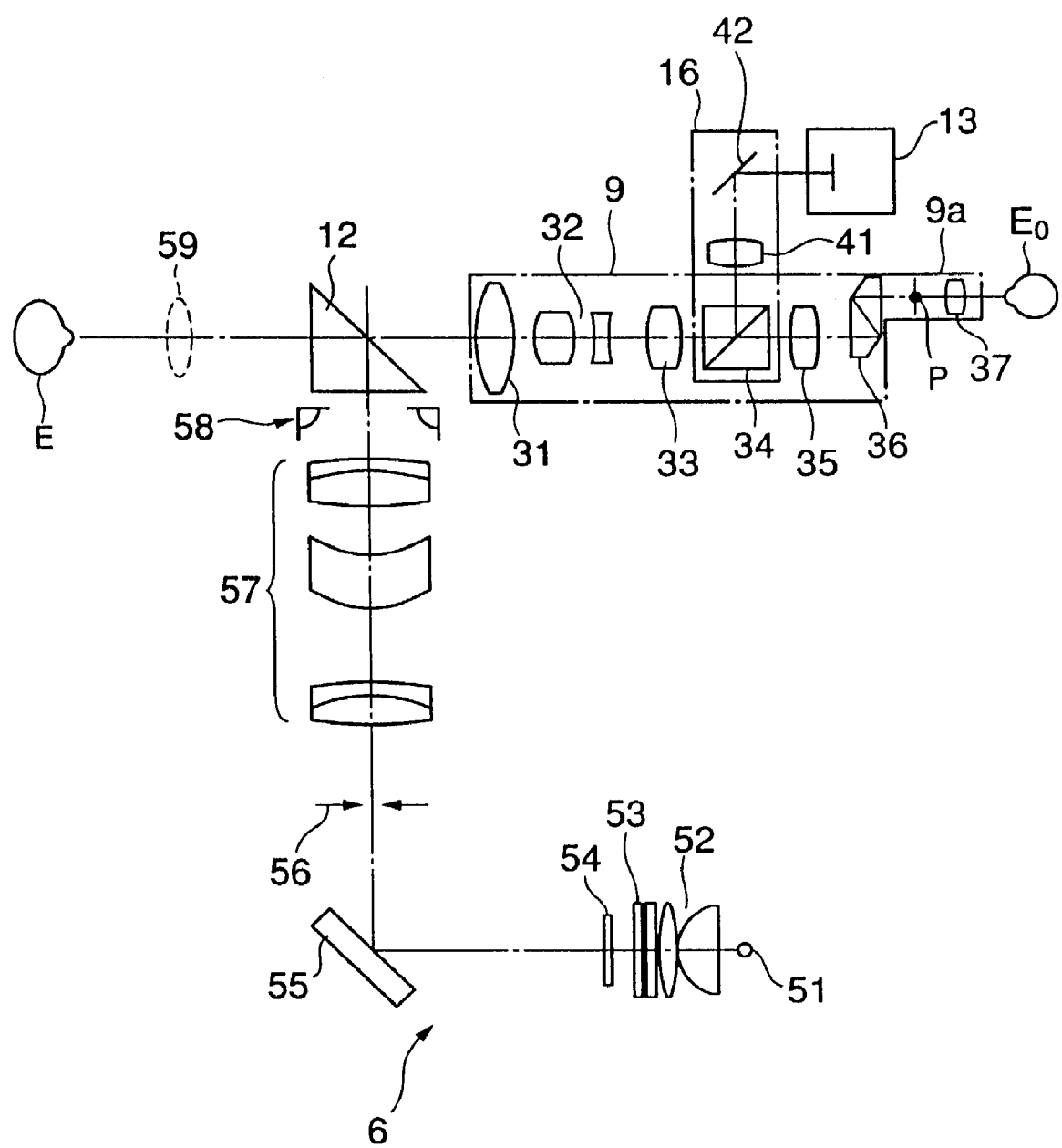
FIG. 17 is a schematic diagram showing the construction of the optical system of the slit lamp microscope of this embodiment.

FIG. 17 schematically shows the optical construction of the slit lamp microscope 1. In this slit lamp microscope 1, the illumination system 6 is provided below the prism 12. The slit lamp microscope 1 has the illumination system 6 arranged below the prism 12 opposed to the eye E to be examined, the observation system 7 arranged perpendicular to the illumination system 6 with respect to the prism 12, the camera attachment 16, and the imaging apparatus 13.

The illumination system 6 has a light source 51 consisting of a halogen lamp or the like, a condenser lens 52 for condensing the light from the light source 51, an infrared filter 53, a color conversion filter 54, a mirror 55 for bending the optical path upwardly by 90 degrees, a slit 56 allowing partial passage of light, a relay lens 57, and a flare cut-off light narrowing down portion (described in detail below) 58 used to observe the fundus of the eye E to be examined, with the prism 12 being arranged above the light narrowing down portion 58.

The observation system 7 is equipped with the prism 12, an objective lens 31, a variable-power optical system 32, a condensing lens 33, a relay lens 35, a prism 36 for bringing the optical path to the eyepiece lens barrel 9a side, and an eyepiece 37 arranged in the eyepiece lens barrel 9a. An image of the eye E to be examined is formed at an image formation point P shown in FIG. 17, and can be observed by the eye E0 of the examiner. The camera attachment 16 has a beam splitter 34 inserted into the optical path of the observation system 7, a condensing lens 41 for condensing the light branched off by the beam splitter 34, and a mirror 42 for bending the light from the condensing lens 41 by 90 degrees to guide it to the imaging apparatus 13.

When the fundus of the eye E is to be observed, a pre-lens 59 is arranged between the prism 12 and the eye E as indicated by the dotted line in FIG. 17 by using an attachment (not shown).

Next, the light narrowing portion 58 will be described in detail with reference to FIGS. 18 through 23.

Figure 18:
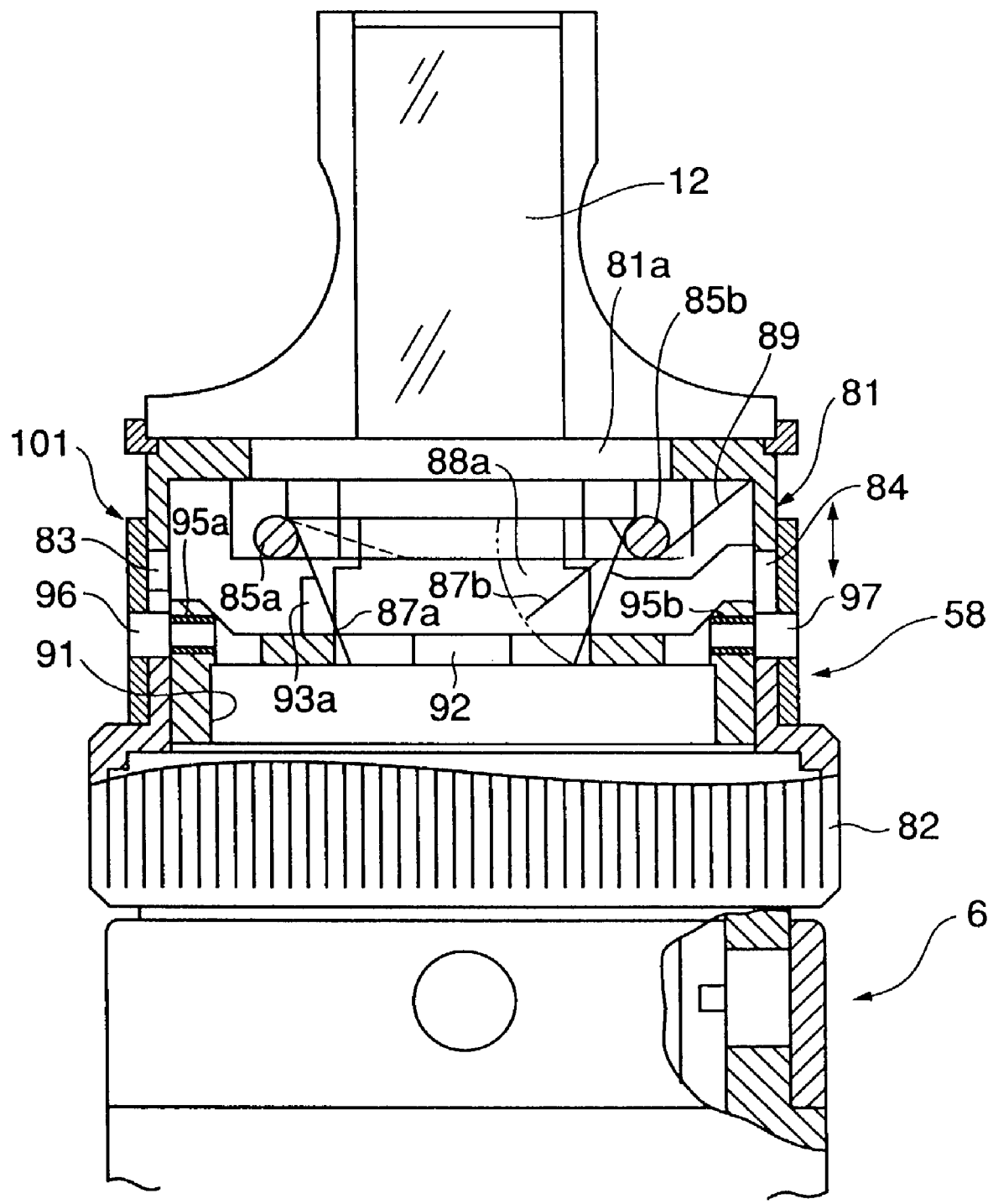
FIG. 18 is a schematic enlarged sectional view of a light (flux) narrowing (diaphragming) portion in the illumination system of this embodiment.
Figure 19:
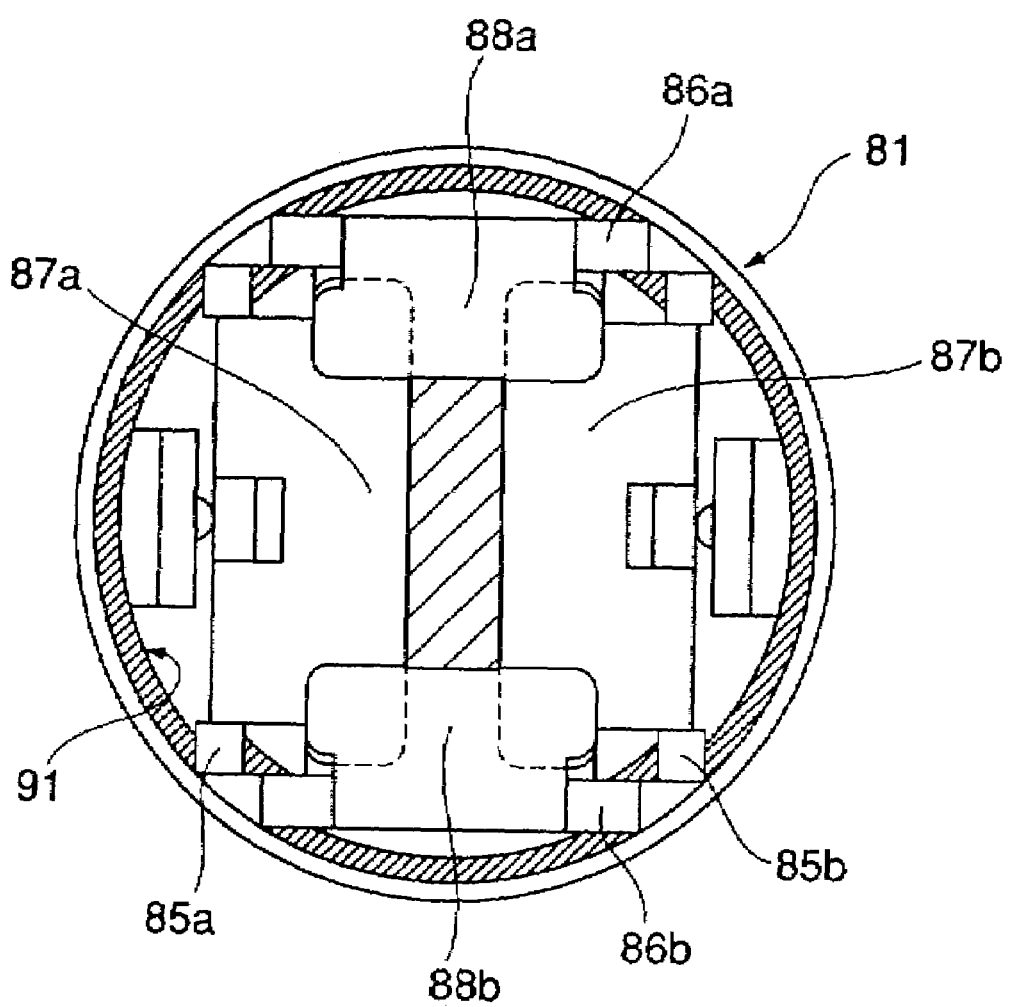
FIG. 19 is a cross sectional view of the light narrowing portion of this embodiment.

As shown in FIGS. 18 and 19, the light narrowing portion 58 has a multiple construction composed of a cylindrical cam support cylinder 81 having at its top an opening 81a, a cam cylinder 91 arranged on the inner side of the cylindrical cam support cylinder 81, and a narrowing operation cylinder 101 arranged on the outer side of the cylindrical cam support cylinder 81, each having at its center the optical path of the illumination system 6.

Figure 20:
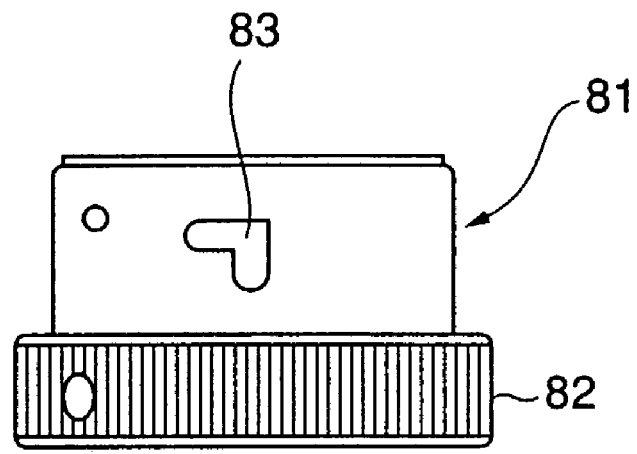
FIG. 20 is a side view of a cylindrical cam support cylinder of the light narrowing portion of this embodiment.

Formed at the bottom of the cylindrical cam support cylinder 81 is an annular mounting portion 82. Further, as shown in FIG. 20, formed in the upper wall surface of the cylindrical cam support cylinder 81 are an L-shaped cam hole 83 consisting of a longitudinal hole and a lateral hole connected together, and a longitudinal hole 84 shown in FIG. 18.

Further, as shown in FIGS. 18 and 19, in the upper portion of the interior of the cylindrical cam support cylinder 81, a pair of rotation support shafts 85a and 85b, spaced apart from each other by a fixed distance, are arranged symmetrically with respect to the optical path of the illumination system so as to be horizontally rotatable. Further, another pair of rotation support shafts 86a and 86b, spaced apart from each other by a fixed distance and perpendicular to the pair of rotation support shafts 85a and 85b, are arranged symmetrically so as to be horizontally rotatable.

A pair of lower narrowing plates 87a and 87b, each substantially rectangular, are mounted to the pair of rotation support shafts 85a and 85b so as to be opposed to each other. Similarly, a pair of upper narrowing plates 88a and 88b, each substantially rectangular, are mounted to the pair of rotation support shafts 86a and 86b so as to be opposed to each other. The pair of upper narrowing plates 88a and 88b are in contact with the upper surfaces of the pair of lower narrowing plate 87a and 87b. Further, the size of the pair of upper narrowing plates 88a and 88b is smaller than that of the pair of lower narrowing plates 87a and 87b.

In the state (narrowing state) in which the pair of lower narrowing plates 87a and 87b and the pair of upper narrowing plates 88a and 88b overlap each other as shown in FIG. 19, the light from the illumination system 6 is narrowed down to the shaded range show in FIG. 19. In FIG. 18, reference numeral 89 indicates a coil spring.

Figure 21:
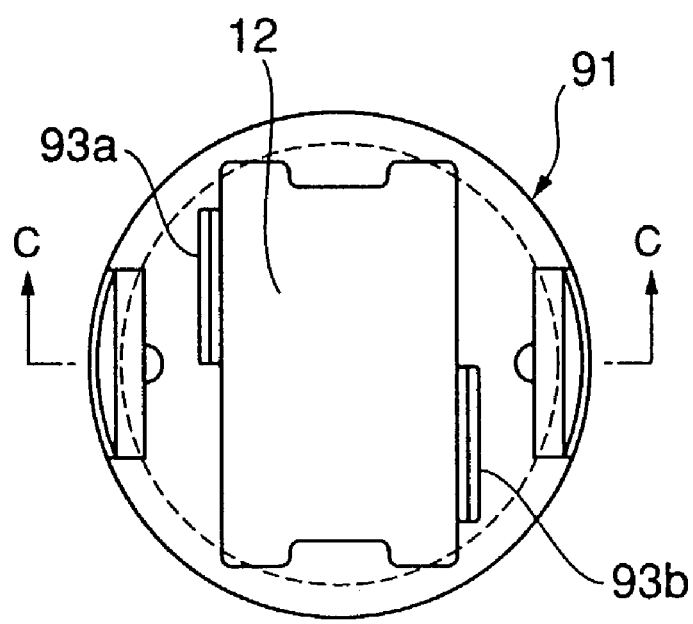
FIG. 21 is a plan view of the cam cylinder of the light narrowing portion of this embodiment.
Figure 22:
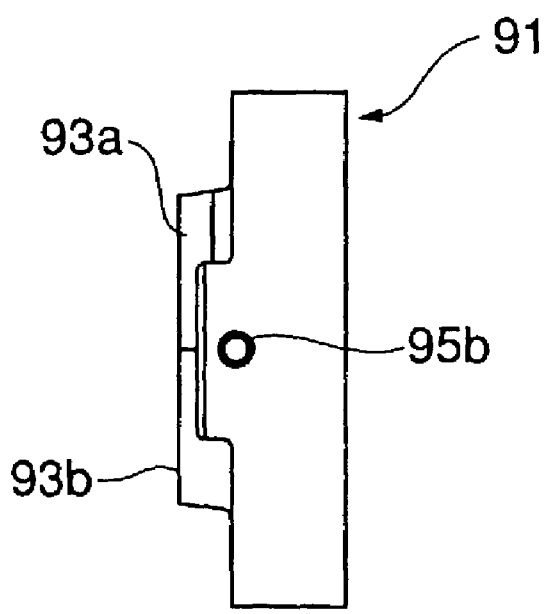
FIG. 22 is a side view of the cam cylinder of the light narrowing portion of this embodiment.
Figure 23:
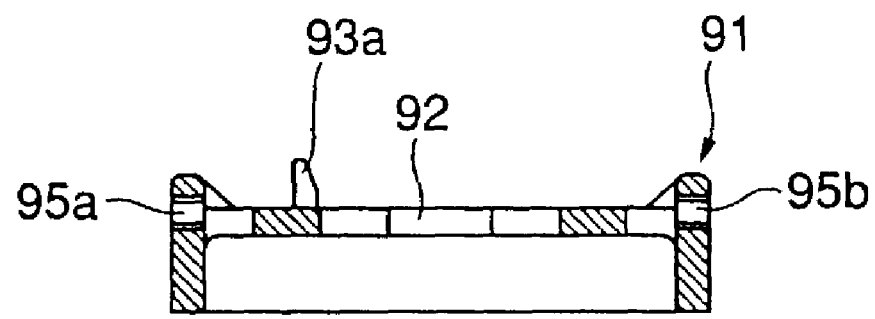
FIG. 23 is a sectional view taken along the line C—C of FIG. 21.

As shown in FIGS. 21 through 23, the cam cylinder 91 has at the center of its top a rectangular light passage hole 92. And, at the longitudinal sides of the light passage hole 92, a pair of push-up members 93a and 93b are arranged symmetrically and protrude upwards.

Further, in the outer periphery of the top of the cam cylinder 91, a pair of connecting protrusions 94a and 94b are arranged symmetrically (by 180 degrees). The pair of connecting protrusions 94a and 94b are equipped with horizontal engagement holes 95a and 95b.

And, as shown in FIG. 18, the narrowing operation cylinder 101 and the cam cylinder 91 are connected together by passing one engagement pin 96 mounted to the wall surface of the narrowing operation cylinder 101 through the L-shaped cam hole 83 to engage it with the engagement hole 95a and passing the other engagement pin 97 mounted to the wall surface of the narrowing operation cylinder 101 through the longitudinal hole 84 to engage it with the engagement hole 95a.

In this construction, the narrowing operation cylinder 101 is raised along the outer periphery of the cylindrical cam support cylinder 81 from the position shown in FIG. 18, and the narrowing operation cylinder 101 is rotated horizontally by an amount corresponding to the lateral hole dimension of the cam hole 83, whereby the pair of push-up members 93a and 93b cause the pair of lower narrowing plates 87a and 87b and further the pair of upper narrowing plates 88a and 88b to rotate upwardly to thereby attain the state shown in FIG. 19, in which the light from the illumination system 6 is narrowed down. This narrowing state is attained for the purpose of preventing flare when the fundus of the eye E is observed by placing the pre-lens 59 in front of the eye E.

When the narrowing operation cylinder 101 is restored to the state shown in FIG. 18 (the narrowing canceling state) by an operation reverse to the above-described one, the light from the illumination system 6 is applied to the eye E by way of the prism 12 without being narrowed down, thereby making it possible to observe a slit image of the cornea of the eye E.

As the cables of this embodiment, apart from the signal transmission cable 23, the image monitor cable 24, and the power cable 25, various cables, such as a control cable for controlling the imaging apparatus 13, are used. Further, the terminal of each cable may be of various types including a connector, plug, pin, and USB terminal.

In accordance with the present invention, an ophthalmologic apparatus is provided in which it is possible to achieve an improvement in operability for the examiner, to mitigate the bother or discomfort for the subject, and to achieve an improvement in terms of outward appearance. Further, it is possible to provide an ophthalmologic apparatus which is compatible with different imaging apparatuses and which helps to prevent the cables from suffering bending and damage.

What is claimed is:

1. An ophthalmologic apparatus comprising:
   an illumination system for illuminating an eye to be examined;
   a support arm for supporting an observation system for observing the eye to be examined and an imaging apparatus mounted to the observation system;
   a base for rotatably supporting the illumination system, the observation system, and the support arm on a protrusive axle shell; a pedestal for supporting the base;
   a chin rest stand for securing the eye to be examined of a subject in position; and
   a table on which the pedestal is installed and to an end of which the chin rest stand is mounted, the ophthalmologic apparatus using cables which are connected at one end to the imaging apparatus and the other ends of which are guided under the table for electrical connection between the imaging apparatus and an image processing system or a control system,
   wherein there is provided a cable hole having an opening through which cables connected to the imaging apparatus come together and which is provided so as to be formed partially along the outer periphery of the protrusive axle shell of the base,
   wherein said cables are routed through a cable routing path having an accommodating groove with a detachable cover provided on the front side of the support arm.

2. An ophthalmologic apparatus according to claim 1, a plurality of corners are provided in the opening constituting the cable hole, and at least two corners positioned near the protrusive axle shell are formed as curved, and wherein displacement of the cables according to a manner of rotation of the observation system and the imaging apparatus with respect to the base, is regulated by the smooth corners.

3. An ophthalmologic apparatus according to claim 2, wherein the ophthalmologic apparatus comprises an arbitrary configuration of said opening and said at least two curved corners are connected as being curved around the protrusive axle shell.

4. An ophthalmologic apparatus comprising:
   an illumination system for illuminating an eye to be examined;

a support arm for supporting an observation system for observing the eye to be examined and an imaging apparatus mounted to the observation system;

a base for rotatably supporting the illumination system, the observation system, and the support arm on a protrusive axle shell;

a pedestal for supporting the base;

a chin rest stand for securing the eye to be examined of a subject in position; and a table on which the pedestal is installed and to an end of which the chin rest stand is mounted, the ophthalmologic apparatus using cables which are connected at one end to the imaging apparatus and the other ends of which are guided under the table for electrical connection between the imaging apparatus and an image processing system or a control system, wherein a cable routing path in which the cables connected to the imaging apparatus comprises an accommodating groove with a detachable cover provided on the front side of the support arm, a cable hole provided in the protrusive axle shell of the base protruding toward the chin rest stand from the pedestal, a cable hole of the chin rest stand, and a cable hole provided in the table, to be passed under the table.

5. An ophthalmologic apparatus according to claim 4, wherein the detachable cover covering the accommodating groove for the cables, which is provided on the front side of the support arm, has a cable passage port situated at a left-hand side position or a right-hand side position in correspondence with an arrangement of the imaging apparatus added to the observation system and a cable connecting position.

6. An ophthalmologic apparatus according to one of claims 1 through 4, wherein the cables are a power cable, an image monitor cable, and a signal transmission cable.

* * * * *